United States Patent [19]

Leistner et al.

[11] Patent Number: 5,237,071
[45] Date of Patent: Aug. 17, 1993

[54] PROCESS FOR PREPARING 2,2′-METHYLENE-BIS(6-(2H-BENZO-TRIAZOL-2-YL)-4-HYDROCARBYL PHENOLS)

[75] Inventors: William E. Leistner, Atlantic Beach, N.Y.; Semyon Moshchitsky, Old Bridge; Mahmut Levent, Cliffside Park, both of N.J.

[73] Assignee: Fairmount Chemical Company, Inc., Newark, N.Y.

[21] Appl. No.: 644,299

[22] Filed: Jan. 22, 1991

[51] Int. Cl.$^5$ .................................. C07D 249/20
[52] U.S. Cl. ........................................ 548/260
[58] Field of Search ............................ 548/260

[56] References Cited

U.S. PATENT DOCUMENTS 4,937,348  6/1990  Kubota ................... 548/259

*Primary Examiner*—Patricia L. Morris
*Attorney, Agent, or Firm*—Richard S. Roberts

[57] ABSTRACT

A method for preparing 2,2′-methylene-bis-[6-(2H)-benzotriazol-2-yl)-4-hydrocarbyl phenols] is disclosed. According to the process (i) formaldehyde, a dialkylamine and a 4-hydrocarbyl-6-benzotriazolyl phenol as monomer are mixed;
(ii) the mixture is heated to a temperature high enough to remove the water produced by the reaction of the mixture;
(iii) thereafter an alkaline catalyst is added with heating for several hours;
(iv) the phenol compound precipitates when the reaction mixture is neutralized and solvent for the salt product of the neutralization reaction is added in an amount sufficient to permit stirring.

The solid product produced is 2,2′-methylene-bis-[6-(2H-benzotriazol-2-yl)-4-hydrocarbyl phenol] having the formula I:

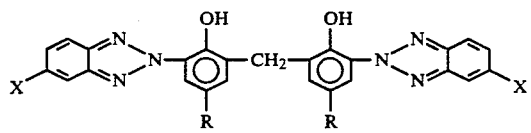

in which each R group is an alkyl group of one to twelve carbons or a cycloalkyl group of five to eight carbons and X is chloro or hydrogen.

20 Claims, No Drawings

PROCESS FOR PREPARING 2,2'-METHYLENE-BIS(6-(2H-BENZOTRIAZOL-2-YL)-4-HYDROCARBYL PHENOLS)

BACKGROUND OF THE INVENTION a) Field of the Invention

This invention relates to an efficient method for preparing methylene bis (6-benzotriazolylphenols), in particular 2,2'-methylene-bis-[6-(2H-benzotriazol-2-yl)-4-(1,1,3,3-tetramethylbutyl)-phenol]. The method allows rapid recovery of very pure product.

b) State of the Art 2,2'-Methylene-bis-[6-(2H-benzotriazol-2-yl)-4-(1,1,3,3-tetramethylbutyl)-phenol] is a known material having utility as an ultraviolet light absorber. It has been the subject of a number of patents including U.S. Pat. No. 4,937,348 (the "'348 Patent"). According to the '348 Patent, alkylidene bisphenols, such as 2,2'-methylene-bis-[6-(2H-benzotriazol-2-yl)-4-(1,1,3,3-tetramethylbutyl)-phenol], may be prepared by (i) reacting a 4-hydrocarbyl-6-benzotriazolyl phenol with a primary or secondary amine and formaldehyde in an inert organic solvent to produce a Mannich base and (ii) reacting the base with itself or a 4-hydrocarbyl-6-benzotriazolyl phenol, preferably in the presence of an alkaline catalyst, such as a lower alkali metal alcoholate, an alkali metal hydroxide or an alkali metal alkaline salt. The reactions are carried out between 20° C. and 200° C., preferably between 30° C. and 150° C. The patent teaches removal of the solvent between steps (i) and (ii) to isolate the crude intermediate.

Preparation of 2,2'-methylene-bis-[6-(2H-benzotriazol-2-yl)-4-(1,1,3,3-tetramethylbutyl)-phenol] is described in Example 3 of the '348 Patent. According to the process 4-(1,1,3,3-tetramethyl)butyl-6-benzotriazolyl-phenol was reacted with a secondary alkyl amine and paraformaldehyde in butanol and heated at reflux temperature for 24 hours. The solvent was distilled off. The resulting Mannich base and 4-(1,1,3,3-tetramethyl)-butyl-6-benzotriazolyl-phenol were dissolved in xylene and sodium methylate was added. The solution was heated under reflux at 140 to 150° C. for ten hours with a stream of nitrogen. The solvent was distilled off. The residue was recrystallized from xylene and then from n-heptane to produce a product melting at 200° C.

In contrast to the prior art processes, the present invention is more efficient and simpler. The entire reaction can be effected more rapidly in a single reaction vessel. Surprisingly, it has been found that by allowing the condensation of the formaldehyde and the amine to proceed before adding a solvent, the time required for the reaction is significantly reduced.

SUMMARY OF THE INVENTION

This invention provides a process for preparing methylene bis (4-hydrocarbyl-6-benzotriazolylphenols) of Formula I, such as 2,2'-methylene-bis-[6-(2H-benzotriazol-2-yl)-4- (1,1,3,3-tetramethylbutyl)-phenol]

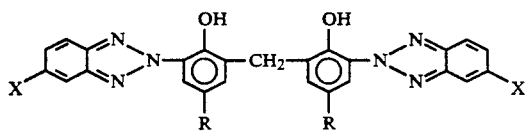

Each R group is an alkyl group of one to twelve carbons or a cycloalkyl group of five to eight carbons; and X is chloro or hydrogen. According to the process of the invention:

(i) formaldehyde, a dialkylamine and a 4-hydrocarbyl-6-benzotriazolyl phenol as monomer are mixed;
(ii) the mixture is heated to a temperature high enough to remove the water produced by the reaction of the mixture;
(iii) thereafter an alkaline catalyst is added with heating for several hours;
(iv) the product is then collected, preferably by neutralizing the reaction mixture and dissolving the salt product of the neutralization reaction by adding a solvent in an amount sufficient to permit stirring. The solid product produced is 2,2'-methylene-bis-[6-(2H-benzotriazol-2-yl)-4-hydrocarbyl phenol].

DETAILED DESCRIPTION OF THE INVENTION

In the practice of the present invention 2,2'-methylene-bis-[6-(2H-benzotriazol-2-yl)-4-(1,1,3,3-tetramethylbutyl)-phenol] and corresponding 4-hydrocarbyl compounds can be prepared rapidly in a single reaction vessel without isolation of intermediates. Very pure products in high yields are achieved with the method of the invention.

The process of the present invention involves reaction of formaldehyde, a dialkylamine and a 4-hydrocarbyl-6-benzotriazolyl phenol with heating in the absence of a solvent. Thereafter an alkaline catalyst and solvent are added. Upon completion of the reaction 2,2'-methylene-bis-[6-(2H-benzotriazol-2-yl)-4-alkyl phenol] is preferably covered by simply neutralizing the alkaline reaction.

More specifically, the formaldehyde used in the reaction is a solid form of formaldehyde. Paraformaldehyde is particularly preferred, but other solid forms may be used.

The amine employed is a secondary amine having the formula $HNR_1R_2$ in which $R_1$ and $R_2$ are independently selected from alkyl groups of three or more carbons, commonly three to eight carbons. In general, the amines are those which are not miscible or soluble in water. The preferred amines are those in which $R_1$ and $R_2$ are the same with the most preferred being those in which $R_1$ and $R_2$ are both propyl, optimally n-propyl.

The monomer used is 4-(1,1,3,3-methylbutyl)-6-benzotriazolyl phenol if 2,2'-methylene-bis-[6-(2H-benzotriazol-2-yl)-4-(1,1,3,3-tetramethylbutyl)-phenol] is the desired product. Alternatively, the appropriate 4-(hydrocarbyl)-6-benzotriazolyl phenol of Formula II below is used to produce the corresponding 2,2'-methylene-bis-(6-benzotriazol-2-yl-4-hydrocarbyl phenol).

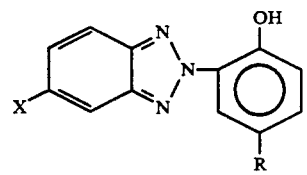

When the three reactants are combined without a solvent and heated with stirring, two moles of the amine rapidly condense with each carbon of the paraformaldehyde. The heat drives off the water formed in its azeotropic mixture with the excess amine. Generally temperatures above about 95° C. to 100° C. are sufficient to cause the water formed to be driven off. Temperatures of 95 to 130° C. are acceptable during this stage of the reaction, although temperatures of 120° C. to 130° C. are preferred.

The heating and stirring of the reactants should continue for a period of time sufficient to permit completion of the condensation of the formaldehyde and the amine and to drive off all water formed in that reaction. Commonly, as little as one or two hours is sufficient, in contrast to prior art processes where as much as 24 hours is required.

The amount of amine used is generally slightly in excess of that required for complete reaction with the formaldehyde. Typically, about two to three moles of amine are used for each mole of carbon in the formaldehyde material used, preferably about 2.5 moles of amine for each mole of carbon. For example, with paraformaldehyde containing three carbons, the molar ratio of paraformaldehyde to amine would be approximately 1:6.

The molar amount of monomer used would in turn also be approximately twice the number of moles of carbon in the formaldehyde. Again, if the paraformaldehyde contains three carbons, the molar ratio of paraformaldehyde to monomer would be approximately 1:6.

Once the condensation reaction is complete and the resulting water has been driven off, there is no need to recover the intermediate product from a solvent since no solvent was employed. Rather, a catalyst is simply added to the reaction mixture, preferably after the mixture has been cooled. The catalyst may be any alkaline catalyst of the type known to be suitable for promoting formation of the bis phenol. The preferred catalyst is sodium hydroxide. Examples of other suitable catalysts are lower alkali metal alcoholates, such as sodium methylate and ethylate; alkali metal hydroxides, such as sodium, potassium and lithium hydroxide; alkali metal amides, such as sodium amide and alkaline salts, such as potassium and sodium carbonate. The amount of the alkaline catalyst is not critical, and small amounts are usually sufficient. A preferred amount is within the range from 0.01 to 5 moles, preferably from 0.1 to 1 mole, per mole of monomer. In the most preferred practice, about 0.1 mole of catalyst is used for each mole of monomer.

Because the reaction mixture resulting from the condensation reaction is very thick, an organic solvent for the reactants is preferably added to the mixture when the catalyst is added. The solvent should be one which is inert to the reactants. It must also have a boiling point which is above that of the catalyzed reaction of the monomer. A solvent with a boiling point above 160° C. (the temperature of the reaction) is preferred. A preferred solvent is 1,2,4-trimethylbenzene. With reactions involving 1 mole of monomer, about 397.5 g of this solvent is preferably used. Various other hydrocarbons, including mineral spirits may also be used as the solvent. Generally, the amount of solvent used ranges from ½ to 3 times the weight of the monomer with about a 1:1.0–1.5 weight ratio of monomer to solvent preferred.

The catalyzed reaction is effected by heating the mixture to a temperature high enough to drive the reaction, generally about 160° C. The reaction is allowed to proceed to completion—generally about six to fourteen hours. A reaction time of 10 hours has been found preferable where 1 mole of the monomer 6-benzotriazolyl-4-(1,1,3,3-tetramethyl butyl)-phenol (i.e. 323 grams) is used.

The mixture resulting from the catalyzed reaction is a semisolid. The desired bis-phenol product may be recovered therefrom using conventional means. In preferred practice, the mixture is cooled and neutralized with a suitable organic acid. Glacial acetic acid is preferred. However, other acids, particularly carboxylic acids such as propionic acid, formic acid and trifluoroacetic acid are also suitable.

In order to remove the salt formed in the reaction of the neutralizing acid, it is preferred that a solvent for the salt be added to the reaction mixture. The bis-phenol product should not be soluble in the solvent selected. The solvent need only be added in an amount sufficient to render the mixture stirrable. Typically, the amount of solvent will be 1 to 5 times the weight of the monomer used. Lower alkanols (i.e., alkanols having one to ten carbons) are suitable solvents for this purpose, with methanol being preferred.

2,2'-Methylene-bis-[6-(2H-benzotriazol-2-yl)-4-(1,1,3,3-tetramethylbutyl)-phenol] or the corresponding methylene bis 4-hydrocarbyl phenol simply precipitates from this reaction mixture and can be recovered by centrifugation as a white powder. High purity yields of greater than 90% and as high as 96% are achieved with the process of the invention.

The following examples are illustrative of the invention.

EXAMPLE I Preparation of 2,2'-Methylene bis (4-t-octyl-6-benzotriazolyl phenol)

15.68 grams (0.52 mole) of paraformaldehyde, 126.7 grams (1.25 moles) of di-n-propylamine and 323 grams (1 mole) of 6-benzotriazolyl-4(1,1,3,3-tetramethylbutyl)-phenol monomer were charged into the reactor. The mixture was heated to about 130° C. with stirring for about 2 hours until no more water was removed.

The resulting mixture was cooled and 4 grams of sodium hydroxide pellets (0.1 mole) and 397.5 grams of 1,2,4-trimethylbenzene (i.e. pseudocumene) were added. The mixture was heated to 160° C. with stirring for about ten hours to remove water and dipropylamine.

The resulting semisolid was cooled to 110° C. 75 grams of glacial acetic acid was added and the mixture was refluxed for 30 minutes. The mixture was then cooled to 50° C. whereupon 600 grams of methanol was added. The mixture was stirred for one hour at 10 to 15° C.

2,2'-Methylene-bis-[6-(2H-benzotriazol-2-yl)-4-(1,1,3-tetramethylbutyl)-phenol] precipitated from the mixture and was collected by centrifugation as a white powder. 313 g of the product was obtained (95% yield) having 99.7% purity by HPLC. The product melted at 194°–196° C.

The product was used in a variety of plastic resins and was found to substantially increase light stability.

EXAMPLE II Preparation of 2,2'-Methylene bis (4-methyl-6-benzotriazolylphenol)

126.7 g (1.25 moles) of dipropylamine, 15.68 g (0.52 mole of paraformaldehyde and 225 g (1 mole) of 4-methyl-6-benzotriazolylphenol were heated at 125–130° C. until no more water was removed. 400 g of pseudocumene and 4 g (0.1 mole) sodium hydroxide were added and the mixture was heated at 160° C. for 10 hours to remove water and dipropylamine. The temperature was lowered to 110° C. and 75 g of glacial acetic acid was added. The mixture was then refluxed for 30 minutes. The mixture was cooled to 50° C. whereupon 600 g of methanol was added. Precipitated product was filtered off. 215 g (yield=93%) of pale yellow product was obtained. It had a melting point of 285-286° C.

What is claimed is:

1. A method for preparing a compound of formula I

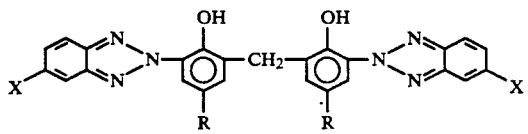

wherein R is an alkyl group of one to twelve carbons or a cycloalkyl group of five to eight carbons and X is chloro or hydrogen comprising:
(a) mixing (i) a dialkylamine of the formula $HNR_1R_2$ wherein $R_1$ and $R_2$ are independently alkyl groups having three or more carbons, (ii) a solid formaldehyde material and (iii) a monomer of formula II

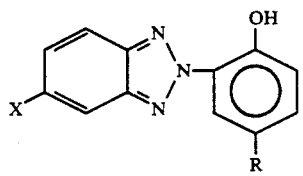

wherein R is an alkyl group of one to twelve carbons or a cycloalkyl group of five to eight carbons and X is chloro or hydrogen, in the absence of a solvent and with heating at a temperature high enough to drive off the water formed in the reaction, and thereafter
(b) adding an alkaline catalyst to the resulting reaction mixture,
(c) stirring the catalyzed mixture at a temperature sufficient to drive the reaction for six to fourteen hours, and
(d) thereafter collecting the resulting compound of Formula I.

2. The method of claim 1 wherein $R_1$ and $R_2$ are propyl.

3. The method of claim 1 wherein $R_1$ and $R_2$ are n-propyl.

4. The method of claim 1 wherein R is 1,1,3,3-methylbutyl.

5. The method of claim 1 wherein the solid formaldehyde material is paraformaldehyde.

6. The method of claim 1 wherein about two moles of dialkylamine are used for each mole of carbon in the formaldehyde material.

7. The method of claim 1 wherein about two moles of monomer are used for each mole of carbon in the formaldehyde material.

8. The method of claim 1 wherein the reactants are heated to 95 to 130° C. during step (a).

9. The method of claim 1 wherein the catalyst is selected from the group consisting of a lower alkali metal alcoholate, an alkali metal hydroxide, an alkali metal amide and an alkaline salt.

10. The method of claim 1 wherein the catalyst is sodium hydroxide.

11. The method of claim 1 wherein about 0.1 mole of catalyst is used for each mole of monomer used.

12. The method of claim 1 wherein a solvent is added in step (b).

13. The method of claim 12 wherein the solvent is pseudocumene.

14. The method of claim 1 wherein step (c) is conducted at at least 160° C.

15. The method of claim 1 wherein the mixture in step (d) is neutralized and a solvent for the salt produced as a result of the neutralization is added, whereby the compound of Formula I precipitates.

16. The method of claim 15 wherein an organic acid is used to neutralize the mixture.

17. The method of claim 16 wherein the organic acid is glacial acetic acid.

18. The method of claim 1 wherein:
(a) the relative proportions of reactants in step (a) are about 2 moles of dialkylamine, about 1 mole of paraformaldehyde having one carbon per mole and about 2 moles of a monomer of formula II and the reactants are mixed and heated to 120° to 130° C. for one to two hours in step (a),
(b) about 0.1 mole of alkaline catalyst per mole of monomer is added in step (b) along with an inert solvent having a boiling point above 160° C.,
(c) the reaction is stirred in step (c) for about ten hours at a temperature of about 160° C., and
(d) the reaction is neutralized with an organic acid in step (d).

19. The method of claim 1 wherein step (a) is conducted for up to about 2 hours.

20. The method of claim 1 wherein step (a) is conducted at a temperature of from about 95° C. to about 130° C.

* * * * *